United States Patent
Purnhagen et al.

(10) Patent No.: US 9,638,586 B2
(45) Date of Patent: May 2, 2017

(54) DYNAMIC WIDE-AREA EARTH THERMAL PROPERTIES AND EARTH AMBIENT TEMPERATURE DETERMINATION SYSTEM

(71) Applicant: Underground Systems, Inc., Armonk, NY (US)

(72) Inventors: David W. Purnhagen, Bayport, NY (US); Chunchuan Xu, Tuckahoe, NY (US); Paul A. Alex, Fairfield, CT (US)

(73) Assignee: Underground Systems, Inc., Bethel, CT (US)

( * ) Notice: Subject to any disclaimer, the term of this patent is extended or adjusted under 35 U.S.C. 154(b) by 539 days.

(21) Appl. No.: 14/196,170

(22) Filed: Mar. 4, 2014

(65) Prior Publication Data

US 2015/0253458 A1    Sep. 10, 2015

(51) Int. Cl.
| | | |
|---|---|---|
| *G01K 1/16* | (2006.01) |
| *G01K 3/06* | (2006.01) |
| *G01K 3/08* | (2006.01) |
| *G01K 3/14* | (2006.01) |
| *G01K 17/00* | (2006.01) |
| *G01K 17/06* | (2006.01) |
| *G01K 17/08* | (2006.01) |
| *G01K 11/00* | (2006.01) |

(52) U.S. Cl.
CPC .................. *G01K 11/00* (2013.01)

(58) Field of Classification Search
CPC . G01K 11/00; G01K 1/16; G01K 3/08; G01K 3/06; G01K 3/14; G01K 17/00; G01K 17/06; G01K 17/08; G06F 2217/36; G06F 2217/80; G09B 23/181

USPC ............... 73/292; 703/2; 702/2, 57, 58
See application file for complete search history.

(56) References Cited

U.S. PATENT DOCUMENTS

| | | | | |
|---|---|---|---|---|
| 3,601,586 A * | 8/1971 | Slavin | .................. | H02H 6/005 377/25 |
| 3,955,042 A * | 5/1976 | Kellow | ................ | H01B 9/0627 165/104.26 |
| 5,543,714 A * | 8/1996 | Blanpain et al. | ........ | G01V 3/40 324/323 |
| 5,991,477 A * | 11/1999 | Ishikawa | ................ | H04L 7/0037 385/24 |
| 6,244,106 B1 * | 6/2001 | Nakura | ..................... | G01V 3/02 374/131 |

(Continued)

FOREIGN PATENT DOCUMENTS

JP      2014202741 A  * 10/2014

*Primary Examiner* — Gail Kaplan Verbitsky
(74) *Attorney, Agent, or Firm* — Haug Partners LLP; William S. Frommer

(57) ABSTRACT

Techniques are described for generating earth sub-surface thermal characteristics over an area include collecting real-time weather data and earth data for a plurality of locations associated with an underground electrical cable and calculating earth thermal properties at the plurality of locations based on the real-time weather data and the measured earth data by an iterative process. The calculated earth thermal properties at two or more of the plurality of locations are interpolated to determine interpolated earth thermal properties at another location associated with the underground electrical cable and a wide-area thermal property map created from at least some of the calculated earth thermal properties and the interpolated earth thermal properties.

12 Claims, 7 Drawing Sheets

(56) References Cited

U.S. PATENT DOCUMENTS

| | | | | |
|---|---|---|---|---|
| 8,640,781 B2* | 2/2014 | Freyer | ............... | E21B 7/06 |
| | | | | 166/385 |
| 8,775,151 B2* | 7/2014 | Algaonkar | ............ | G01K 11/32 |
| | | | | 385/13 |
| 2002/0169558 A1* | 11/2002 | Smith | ............... | G01V 3/15 |
| | | | | 702/5 |
| 2004/0109651 A1* | 6/2004 | Lancaster | ............ | G01K 11/32 |
| | | | | 385/101 |
| 2009/0097015 A1* | 4/2009 | Davies | ............... | G01K 11/32 |
| | | | | 356/73.1 |
| 2009/0262781 A1* | 10/2009 | Shumaker | ............ | G01K 1/08 |
| | | | | 374/141 |
| 2009/0279582 A1* | 11/2009 | Yakymyshyn | ......... | G01B 17/04 |
| | | | | 374/119 |
| 2011/0210844 A1* | 9/2011 | Dey | ............... | G08B 13/1445 |
| | | | | 340/521 |
| 2011/0218790 A1* | 9/2011 | Algaonkar | ............ | G01K 11/32 |
| | | | | 703/13 |
| 2012/0199368 A1* | 8/2012 | Freyer | ............... | E21B 7/06 |
| | | | | 166/385 |
| 2015/0242970 A1* | 8/2015 | Avey | ............... | G06Q 10/067 |
| | | | | 705/314 |
| 2016/0076945 A1* | 3/2016 | Wen | ............... | G01K 7/34 |
| | | | | 374/184 |
| 2016/0212952 A1* | 7/2016 | Runge | ............... | A01G 25/16 |
| 2016/0364509 A1* | 12/2016 | Zhang | ............... | G06F 17/5009 |

* cited by examiner

DYNAMIC WIDE-AREA EARTH THERMAL PROPERTIES AND EARTH AMBIENT TEMPERATURE DETERMINATION SYSTEM

BACKGROUND

1. Field of the Invention

This invention is related to a dynamic wide-area subsurface earth thermal map, which can improve the accuracy of underground power cable ratings in general as well as dynamic rating systems and fluid leak detection systems for power cables in particular. A dynamic wide area subsurface earth map can also be utilized to improve the performance of oil and gas pipeline monitoring and leak detection systems, heat pump analysis, etc.

2. Description of the Related Art

The electrical power transmission capability of underground cables is limited by the maximum allowable conductor temperature. If the conductor temperature exceeds the maximum allowable conductor temperature, the cable dielectric will be damaged and deteriorate and ultimately fail. The conductor temperature results from heat generated by the cable and the ability of the surroundings to dissipate this heat, thus raising the temperature above earth ambient temperature at the depth of the cable.

Typically, the worst-case earth thermal conditions are estimated and used to calculate the "static" or "book" rating for underground cables. Generally, the conservative and worst-case thermal conditions are not realized in practice and the underground cable current capacity is higher than the conservative "book rating" using estimated parameters.

How efficiently the surroundings (native soil, thermal backfill, or concrete duct bank) can take heat away from the cable is determined by the soil temperature, soil thermal resistivity, and soil volumetric heat capacity. One way to obtain soil temperature is to measure it with discrete temperature sensors buried in the ground. Soil thermal resistivity and volumetric heat capacity can also be measured in situ by commercially available instruments. However, since it is costly to install temperature sensors in the ground and to maintain and repair them, discrete earth temperature sensors are usually limited to only a few locations for a typical power cable system and usually only for higher voltage heavily loaded circuits. Therefore heretofore arbitrary assumptions must be made regarding earth temperatures between discrete measurement points. Discrete measurement points are also subject to failure, and without a reliable means to replace this data, real-time dynamic systems can be seriously compromised. Taking discrete soil samples several feet below the ground surface for thermal resistivity and volumetric heat capacity measurements is also expensive and measurements can be unreliable due to the fact that thermal resistivity and volumetric heat capacity change with soil temperature and weather dependent moisture content. In addition, soil thermal properties can change along the cable route.

In recent years, Distributed Temperature Measurement Systems (DTS), which provide a thermal profile along a fiber installed under the cable jacket in adjacent ducts or otherwise along the cable route have also been utilized-either alone or in combination with discrete temperature sensors.

More efficient and practical ways to more closely estimate soil temperature, soil thermal resistivity, and soil thermal volumetric capacity without installing, maintaining and reading a large quantity of underground sensors is needed to operate underground power systems safely which are typically spread out over a large geographical area(cities), reliably, and efficiently.

Disclosed is a system that estimates soil temperatures as a function of depth below the surface over a wide area using an iterative process to "identify" the soil temperature using a minimum of sub-surface soil temperature measurement data in conjunction with weather data from weather stations or weather services. In the process this system also uses an iterative process to "identify" soil thermal resistivity and soil thermal capacitance which are also used by the dynamic modeling system. The system continuously "identifies" or updates the three parameters: soil temperature, soil thermal resistivity, and soil thermal volumetric heat capacity in real-time. With these real-time data, a large geographical dynamic thermal contour map at any depth can be created to aid power utility companies and other users in rating their underground power cable systems more accurately and in real-time in a wide geographical area utilizing a limited number of weather/earth/load real-time measurements and data.

One method for assessing underground cable ratings for a discrete cable system based on Distributed Temperature Sensing (DTS) is presented in an article entitled "Assessment of Underground Cable Ratings Based on Distributed Temperature Sensing", *IEEE Transactions on Power Delivery*, October 2006 by H. J. Li et al. Hot spots of the power system are identified and located with the DTS sensor. Information and data on cable construction and circuit installation on the hot spots is then collected. Cable loading and DTS temperature data is collected for estimating the unknown parameters such as the soil thermal resistivity. The Finite Element Method (FEM) technique is utilized for solving two dimensional differential thermal equations to obtain the final rating results.

Another model for estimating earth ambient temperature using dynamic weather data input is proposed in an article entitled "Method for Rating Power Cables Buried in Surface Troughs", *IEEE Proc-Gener, Transm, Distrib*, Vol, 146, No. 4. July 1999 by P. L. Lewin et al. Earth ambient temperature is calculated using weather data such as, ambient temperature, wind speed, solar intensity, etc based on assumed constant thermal parameters.

However, thermal parameters are not updated (or "identified") continuously in either of the above references. In the real world, these parameters change with environmental conditions. For instance, rain can increase moisture content in the soil resulting in a lower thermal resistivity.

SUMMARY OF THE DISCLOSURE

Advantages of the disclosed techniques include providing a dynamic as well as more accurate systems, devices, and methods of determining the real-time thermal conditions and properties of the earth over a wide area where underground power cables and other devices are buried to help system owners utilize these systems more safely and efficiently. After the earth thermal conditions and properties are "identified", the maximum allowable power the system can deliver, i.e, the rating is calculated. The ratings calculated using earth conditions determined by this method may be higher or lower than the ratings based on the case of estimated thermal conditions, but they will be more accurate. Furthermore, the system can also compute conductor temperature in real-time and send alarms to the control center before the conductor temperature exceeds the allowable maximum operating temperature.

The disclosed techniques and calculations can be used to determine either static ratings or dynamic ratings for electrical conductor. A static rating provides a single number for current carrying capacity of an electrical cable for a given set of conditions—ambient temperature, earth thermal characteristics, etc.—associated with the conductor. A dynamic rating is constantly changing with changes in the set of conditions acting on the electrical cable.

In one aspect, the method of determining earth subsurface thermal characteristics over an area includes collecting real-time weather data and earth data for a plurality of locations associated with an underground electrical cable and calculating earth thermal properties at the plurality of locations based on the real-time weather data and the earth data by an iterative process. The calculated earth thermal properties at two or more of the plurality of locations are interpolated to determine interpolated earth thermal properties at another location associated with the underground electrical cable and a wide-area thermal property map created from at least some of the calculated earth thermal properties and the interpolated earth thermal properties.

In another aspect, the method includes superimposing heat sources and heat sinks affecting the earth thermal properties associated with the underground electrical cable into the wide-area thermal property map and continuously providing real-time weather data and earth data to provide a wide-area dynamic thermal 3-dimensional map of earth thermal properties at depths at the plurality of locations. The earth thermal properties can include soil volumetric heat capacity and soil thermal resistivity.

The iterative process for calculating the earth thermal characteristics includes, for one or more selected locations from the plurality of locations, performing the steps of calculating earth ambient temperature data based on values of earth thermal properties and the real-time weather data and collecting real-time measured earth ambient temperature from earth ambient temperature measurement devices. The calculated earth ambient temperature data is compared with the measured earth ambient temperature data and an error value determined based on the comparison. Based on the determining step, values for the earth thermal properties are adjusted and the calculated earth ambient temperature data is recalculated using the adjusted values for earth thermal properties. The process of comparing the calculated earth ambient temperature data with the real-time measured earth ambient temperature, adjusting the earth thermal properties, and recalculating the calculated earth ambient temperature data is repeated until the error value is within a predetermined value.

Power ratings including safe current carrying ampacities for the underground electrical cable can be determined based on the generated wide-area dynamic 3-dimensional map and warning signals can be generated when changes in earth thermal properties result in changes in earth thermal properties affecting the safe current carrying ampacity of the underground electrical cable.

An advantage of the disclosed technique can be to estimate the large-area earth ambient sub-surface temperature profile using primarily weather data input with earth parameters derived from a limited number of weather stations equipped with sub-surface soil temperatures alone, or weather stations alone, or data from weather service providers.

Another advantage of the disclosed technique can be to provide a measurement and calculation procedure to derive earth parameters using real-time weather conditions and earth temperatures.

Another advantage of the disclosed technique can be to calculate the cable ratings based on the derived earth properties and calculated and measured earth temperature.

Another advantage of the disclosed technique can be to build a wide-area earth thermal contour map at various depths based on the derived earth parameters and ambient air and other weather data input. The wide-area earth contour will allow power utility companies to assess the status of their underground power cable systems network in the wide area whether or not circuits have discrete temperature sensors.

Another advantage of the disclosed technique can be to fully utilize "DTS" systems and other conductor or cable surface temperature measurements by establishing a virtual earth ambient thermal profile along the axis of the cable.

The various features are pointed out in the claims annexed to and forming a part of the disclosure. Advantages of the present invention are made clear during the course of a detailed description of the novel system set out herein below.

DETAILED DESCRIPTION

Hereinafter, the present invention will be described in detail with reference to the above drawings. It should be noted that terms and vocabularies used herein should not be construed as limited to general and dictionary meanings.

Figure 1:
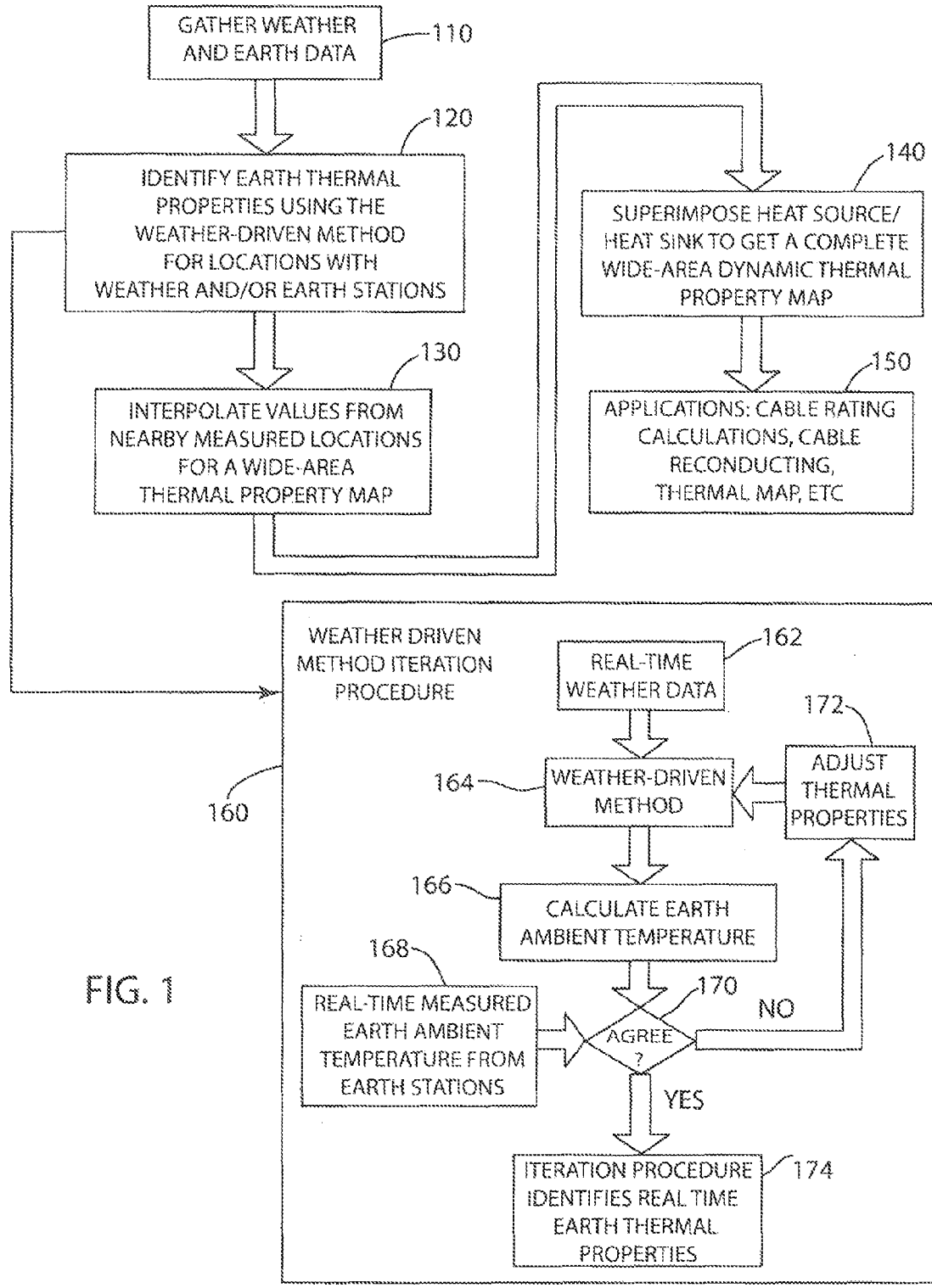
FIG. 1 is a block diagram of the system according to the present invention for dynamically monitoring wide-area thermal properties by feeding real-time weather and earth data using a weather-based technique.

Referring to FIG. 1, the present technique relates to a method for estimating real-time wide-area earth thermal conditions using real-time measured temperature data, weather data. Weather data and earth data are collected at step 110 in real-time by weather stations or provided by weather data service providers for locations related to an underground cable. Real-time earth data come from earth ambient temperature measurement devices such as an earth tree or Distributed Temperature Sensors (DTS). Gathered weather data may be provided to the weather driven calculation module at step 120 resulting in calculated earth ambient temperature data by an iterative process described in more detail below. By comparing the calculated earth ambient temperature data with the measured earth ambient temperature data in real-time, earth thermal properties can be identified for the locations with weather and earth data. In step 130 the real-time calculated values from nearby locations are interpolated so that a wide-area thermal property map can be created utilizing Geographic Information System (GIS) or some other mapping technique. Next in step 140 by superimposing heat sources and heat sinks affecting the underground cable into the map and continuously feeding real-time weather and earth data into the real-time model, a complete wide-area dynamic thermal 3-dimensional map is achieved, which in step 150 can be used for applications such as power cable ratings, system planning, pipe fluid leak detection. etc. With real-time earth conditions known, real-time cable ratings can be calculated. Warning signals can be generated upon the occurrence of dangerous earth conditions due to, for example, extremely dry and hot weather. In response, underground power delivery systems can be operated for maximum safe ampacities (current carrying capacity).

Figure 4:
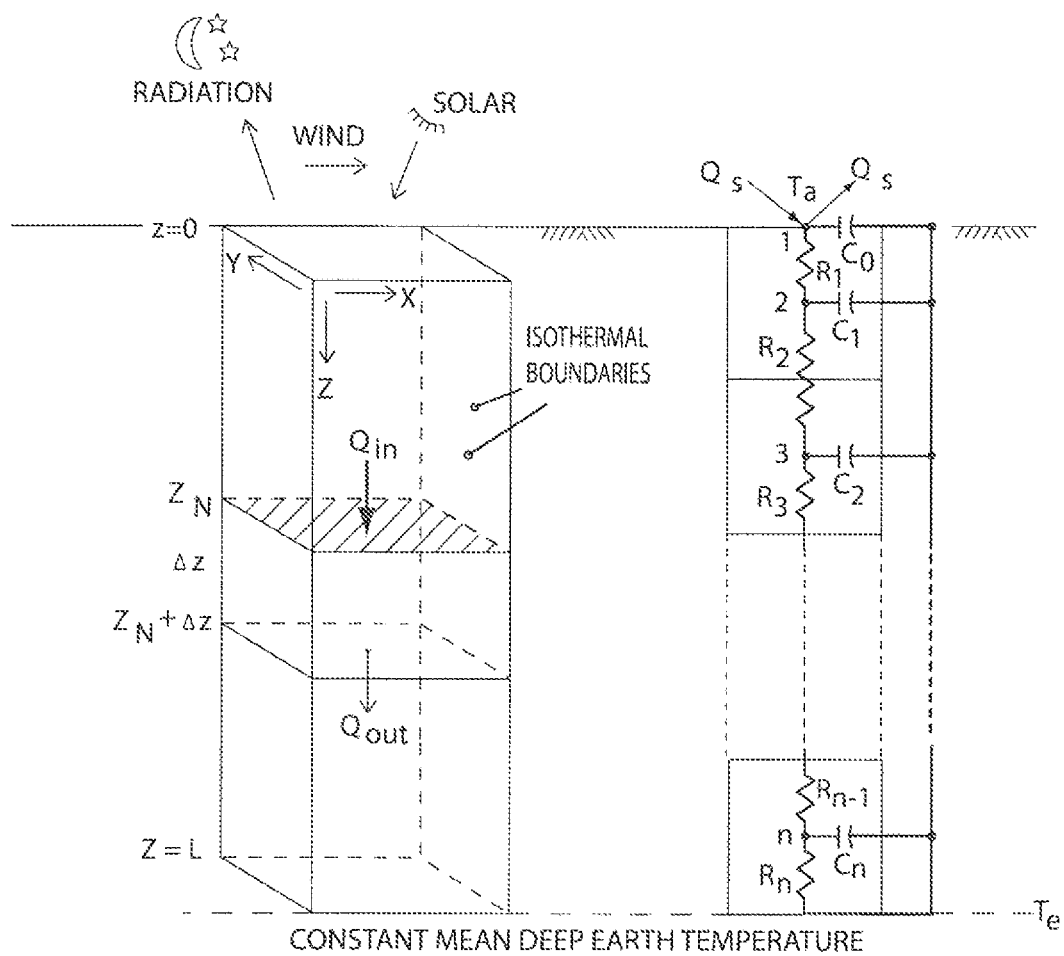
FIGS. 4A-4B are a diagram illustrating a weather-driven model that can be used to calculate earth ambient temperature with weather data input.

As discussed above, the weather-driven method for determining earth thermal properties in step 120 is achieved by an iterative process 160. In the iterative process real-time weather data are collected at step 162. The real-time weather data are provided at step 164 for a location to a weather-driven calculation for determining an earth ambient temperature at step 166. At step 168 actual real-time measured earth ambient temperature is collected from earth stations including earth trees and/or DTS for the location. At step 170 the actual real-time measured earth ambient temperature collected in step 168 is compared to the calculated earth ambient temperature determined in step 166. If the difference between the real-time temperature and the calculated temperature is not within a predetermined error value then the earth thermal properties, including values for soil volumetric heat capacity and soil thermal resistivity, used in the weather-driven calculation are adjusted at step 172. This iterative comparison at step 170 continues until the real-time earth ambient temperature and the calculated earth ambient temperature are within the predetermined error value. If so, at step 174 the weather-driven method identified the real-time earth thermal properties. A method for calculating earth ambient temperature using the real-time weather data and the earth thermal properties is discussed further in regards to FIG. 4.

Global Earth Condition Estimation

Before turning to a description of the details of the system it is helpful to understand the concept of wide area earth condition estimation and how such conditions can affect an underground power delivery system. The underground power delivery system is widely distributed and due to complex installation conditions and the fact that the system is buried underground it can be extremely expensive to install and monitor temperature sensors to establish the appropriate earth ambient temperature throughout the whole system. High Voltage transmission cable systems can have a number of discrete temperature sensors installed on the cable jacket or cable pipe and infrequently a remote earth temperature sensor. The bulk of the underground Transmission and Distribution system is the Distribution component at voltages below 100 kV and standard practice is not to install sensors on the cable jacket, etc. Temperature sensors, such as thermocouples, are installed at selected locations along the cable route identified by analyzing plan profile drawings augmented by soil stratigraphy information and generic or discrete soil thermal property survey data to identify where critical hot spots may exist. Without a wide-area earth estimation model, most sections of the underground power cable system lack temperature and soil thermal property data for assessing their ampacities and rely almost exclusively on estimates that create significant uncertainty and can lead to catastrophic failure at the most inappropriate time (contingent loads during environmentally extreme dry/hot conditions). As an example, referring to FIG. 2, cable route 1 has existing earth stations at locations A, E and G. Cable 2 has no earth stations and cannot be easily retrofitted due to below grade permitting and route access. In contrast, above grade weather stations can be readily added within the region of interest at locations B, C, D and F. Using a commercial GIS engine, a relatively detailed thermal contour map of the region can be generated using interpolation algorithms. Not only is an improved thermal profile of cable 1 obtained, but a reasonably accurate thermal profile of cable 2 is generated for the underground power delivery system. There are several major factors that determine the system ampacity, such as cable current loading, cable construction, installation, thermal properties of the surrounding soil, the ambient temperature, etc. Of these factors, soil thermal properties and ambient temperature vary continuously with weather. In other words, the system ampacity is dynamic. With the wide-area earth condition estimation system, soil thermal properties and ambient temperature in a large area can be estimated thus the ampacity of the various discrete power cable systems in that wide area can be assessed in real-time even when there are no temperature sensors for certain routes or temperatures sensors are out of service. Furthermore, by accumulating data for a period of time, the thermal properties of areas monitored can be identified, and this data can be provided to optimize cable design layout, construction and installation to maximize cable ampacities of new power cable systems.

Temperature Sensors

Point temperature sensors as well as distributed temperature sensors can be used for earth temperature measurements. Other types of sensing devices can also be used for temperature measurements for the earth condition estimation.

Figure 3:
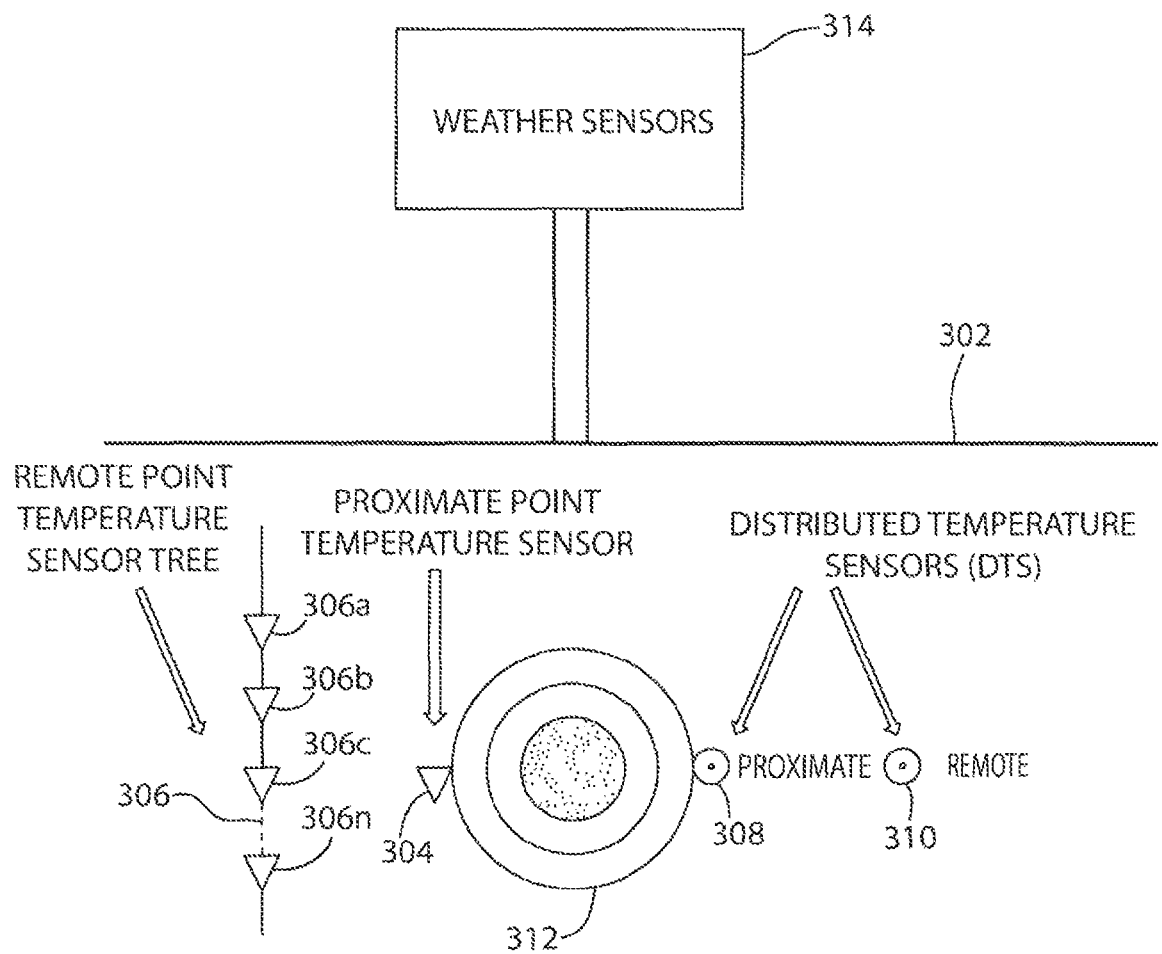
FIG. 3 is a diagram illustrating different types of temperature sensors and earth trees.

Referring to FIG. 3, an advantage of point temperature sensing devices 304 is that such sensors can be easily installed on critical locations and several point temperature sensors 306a . . . 306n can be installed at one particular location at different depths forming an "earth tree" 306 to collect soil temperatures at different depths below ground level 302. The condition estimation system is more robust and accurate with point temperature sensors 304 than distributed temperature sensors (DTS) because there are multiple sensors 306a . . . 306n at one location. Additionally, the deployment of temperature sensors at different depths makes thermal property estimation more accurate because heat flow can be observed more closely leading to more accurate determination of thermal property parameters than with a DTS system. Also, flexibility is another advantage for point temperature sensors when dealing with critical locations. Point temperature sensors can be installed at different depths and different spacing relative to the cable 312 surface to more closely define and monitor a critical hot spot.

One advantage of DTS 308, 310 is that such systems can monitor the temperature profile continuously along the whole cable route. Cable hot spots can be identified and monitored from the distributed temperature profile. A disadvantage of a DTS system is that the DTS measures the cable core or cable shield. While another fiber can be installed in an empty duct or in the cable trench, the relationship of the additional fiber to ambient earth temperature is likely to be unknown. So a cable rating is still based on an assumed earth ambient temperature and the thermal resistance from cable surface to earth ambient is assumed. A second disadvantage of the distributed temperature sensors is that it is prone to a common mode failure; that is, once the DTS sensor fails, the estimation system will stop.

To take advantage of both types of temperature sensors—DTS and point temperatures sensors—for cable routes where the distributed temperature sensor is installed, the distributed temperature sensor is used for establishing the temperature profile of the cable along the cable route. From the temperature profile, hot spots can be identified. Additional point temperature sensors can be installed at these hot locations for discrete soil thermal condition estimation. If these point temperature sensors are monitored in real-time, then the soil thermal property can be identified in real-time at these locations. However, there is no assurance these thermal cross sections will remain the hottest, that is, the locations that are most likely limiting cable ampacity. If the DTS measured hot spot moves due to changes in cable loading, of soil moisture, temperature, or adjacent heat source or sink, then in the absence of a wide area earth model additional point temperature sensors may need to be installed to establish the hot spot thermal property in real-time. The point temperature sensors if not at the DTS identified hotspots can be calibrated and used as a default for the system if the DTS fails or is otherwise out of service.

Weather-Based Wide-Area Earth Ambient Temperature and Thermal Property Estimation The earth ambient temperature is a component of a dynamic rating system. When an earth sensor fails or is electrically noisy, the systems may be compromised. The present technique discloses a method for replacing missing or noisy earth ambient data using a weather-driven model in conjunction with available data from adjacent earth condition estimation systems. Information can be interpolated between earth estimation systems (thus the term 'Wide-Area') rather than depend strictly on isolated earth sensors associated with each earth condition system. The reliability and accuracy of the earth condition estimation system could be substantially improved by using interpolation formulae thus providing continuous subsurface earth temperature data over a wide area.

Description of the Dynamic Earth Temperature Model

Earth (soil) ambient temperature annual and daily fluctuations are determined mainly by variations in air temperature, solar radiation, wind speed, and cloud covering ratio. Normally, heat is transferred into the earth in summer and out of the earth in winter.

A one-dimensional distributed parameter model such as depicted in FIG. 4A is sufficiently accurate for the temperature estimation provided that the vertical increments are small. Finite difference or finite element techniques could also be used. The model consists of a square heat flow tube extending vertically from the earth's surface to some distance below the surface where about 99% of the cyclic thermal wave has been dissipated and can be considered a constant temperature, Te. This depth is typically in the 8-15 meter range. The vertical rectangular surfaces of the heat flow tube can be considered adiabatic as adjacent soil properties and conditions are not expected to vary much. The heat balance of any incremental element (z) can be written as:

$$Q_{in} = Q_{out} + Q_c = Q_{out} + C_z \frac{dT_z}{dt} \tag{1}$$

Where:
$Q_{in}$=heat flow into the element, W
$Q_{out}$=heat flow out of the element, W
$Q_c$=heat absorbed by the thermal capacity of the element, W
$C_z$=thermal capacitance, W-s/° C.
$T_z$=temperature of the element, ° C.
t=time, Thereby a distributed ladder network of FIG. 4B can be generated where:

$$R_z = \frac{\rho \Delta z}{A} \tag{2a, 2b}$$

$$C_z = C_v V_z$$

Where:
$\rho$=thermal resistivity of element, ° C.-m/W
$A=\Delta x^* \Delta y$=cross-sectional area of element, m$^2$
$\Delta z$=height of element, z
$C_v$=volumetric thermal capacity, $$\frac{w-s}{° C.-m^3}$$

$V_z=\Delta x^* \Delta y^* \Delta z$=volume of element, m$^3$

A system of linear differential equations that describes the model can be written as follows:

$$\dot{T}_1 = T_1\left(-\frac{1}{R_1 C_1}\right) + T_2\left(\frac{1}{R_1 C_1}\right) + AH_S \tag{3a}$$

$$H_s = H_{sol} + H_{con} + H_{lw}$$

$$i = 2 \ldots (n-1)$$

$$\dot{T}_i = T_{i-1}\left(\frac{1}{R_{i-1} C_i}\right) + T_i\left(-\frac{1}{R_{i-1} C_i} - \frac{1}{R_i C_i}\right) + T_{i+1}\left(\frac{1}{R_i C_i}\right) \tag{3b}$$

$$\dot{T}_n = T_{n-1}\left(\frac{1}{R_{n-1} C_n}\right) + T_n\left(-\frac{1}{R_{n-1} C_n} - \frac{1}{R_n C_n}\right) + \frac{T_s}{R_n C_n} \tag{3c}$$

where $\dot{T}_n$ is the derivative $dT_n/dt$ which is approximated by $\Delta T_n/\Delta t$, and $H_s$ is the heat flowing in and out of the surface including $H_{sol}$, solar heat, $H_{con}$, convective heat flux, and $H_{lw}$, long-wave radiation heat. A solution for the present temperature at each node $T_n$ is then obtained by adding $\dot{T}_n$ to the temperature array $T_{n-1}$ of the previous time step. The method of integrating or marching forward is dependent on the accuracy desired. However, a two-step enhanced Euler technique may be sufficiently accurate. The procedure is to march two steps forward and average the results:

$$T_{n,t2} = T_{n,t1} + \frac{(k_1 + k_2)h}{2} \tag{4}$$

$$k_1 = \dot{T}_{n,t1};$$

$$k_2 = \dot{T}_{n,t1+h};$$

$$h = t_2 - t_1$$

More accurate integration methods such as a 6 step Runge-Kutta procedure could also be used. The conditions at the earth's surface also can be considered. The dominant driving function is the ambient air temperature. Additional factors are solar heat loading $Q_s$, and radiation $Q_r$. and wind convection. Radiation, sometimes referred to a "long wave radiation" tends to cool the earth at nighttime when cloud cover is non-existent or trap heat when cloud cover is high. The wind velocity (∂w) can be obtained via an anemometer. The ambient air temperature $T_a$ is easily obtained with a shielded temperature sensor incorporated in the weather station. Solar radiation can be measured directly by a pyranometer incorporated in the weather station. This is preferred over a mathematical prediction for the particular latitude and longitude as it accounts for cloud interference or blockage by nearby structures. The long wave radiation can be measured by radiation meters pointed at both the sky and the ground surface or can be calculated using the following equation:

$$H_{lw} = \beta(T_{air}^4 - T_{gr}^4) - \frac{X - 0.2}{0.8}(170.9 - 0.195\beta T_{air}^4) \quad (7)$$

where $T_{air}$ is the ambient air temperature, $T_{gr}$ is the ground surface temperature, β is the Boltzmann constant, and X is the daily cloud cover factor. Convective heat flux can be computed using the following equation:

$$H_{con} = k(T_{gr} - T_{air})$$

$$k = 6 + 4.6 V_w \quad (8)$$

Note in the above Equations 7 and 8, some parameters may need adjustments to get best results, which can be done after some data are accumulated. Weather data can be obtained directly from weather station measurements or from weather service providers. Cables are frequently buried under pavement and properties of the pavement may be included in the first several elements of the model. This is readily accomplished by changing the properties of the elements corresponding to the pavement geometry. If knowledge of certain soil strata is also available then those properties could be modified in layers.

Temperature Estimation Initialization

The model is constructed by initially using measured earth parameters, namely resistivity (ρ) and volumetric thermal capacity ($C_v$) or previously estimated earth parameters using the method described below. When installing the subsurface earth tree it may be beneficial to retain soil samples and perform laboratory analysis to determine the values of ρ and $C_v$. In the absence of measured parameters, guidelines for selecting these parameters can be found in many published sources (Appendix B of the *National Electrical Code* (B.310.15(B)(2)), G. S. Campbell Biophysical Measurements and Instruments, Measurement of Soil Thermal Properties and Heat Flux, Volumetric heat capacity, Wikipedia). A suggested range of values are shown in Table 1:

TABLE 1

| Thermal Properties | Dry | Wet |
|---|---|---|
| Thermal resistivity (Km/W) | 1.2 | 0.6 |
| Volumetric heat capacity (MJ/Km³) | 1.2 | 4.18 |

An initial deep earth temperature $T_e$ can be estimated from historical weather information and the average yearly air temperature can be used as an initial estimate. It is possible to initialize all nodes in the model at the deep earth temperature and let the parameter adjustment feedback loop automatically adjust parameters. However, due to long time constants it may take several months or up to ½ year before the modeled temperatures begin tracking the measured values. Another method of initialization is to adjust air temperature, solar heat loading and radiation so that the calculated temperatures closely match the measured subsurface temperatures when a steady state solution of Equations (3) is obtained.

Adaptive Earth Thermal Property Identification Method

Figure 5:
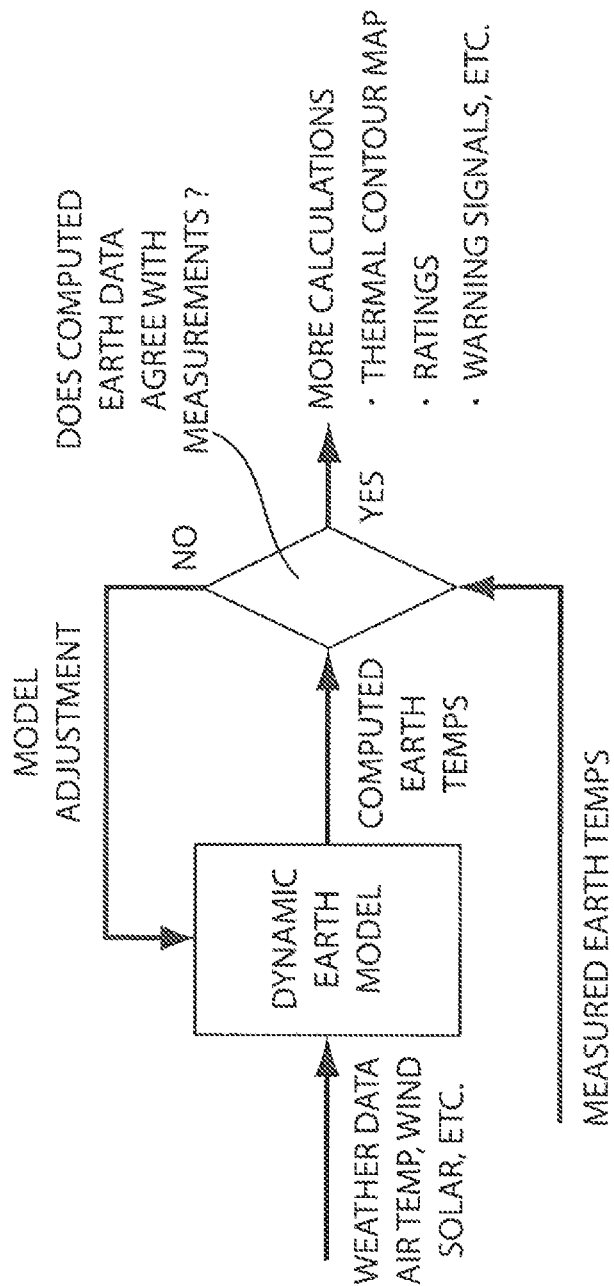
FIG. 5 illustrates using a weather-driven model to estimate earth thermal properties using weather data and measured earth ambient temperature input.

The earth model described above can not only be used to estimate the earth ambient temperature but also used for estimating earth thermal properties. An adaptive or learning based modeling scheme is used to continuously update the model such that weather dependent parameters are considered. The scheme is diagrammatically depicted in FIG. 5. The forcing functions that drive the model, consisting of measured air temperatures, wind speed, solar input and radiation are provided to the model. The data can be processed according to Equations (3) to compute earth temperatures at each incremental node at each time step. The computed earth temperatures can be compared to measured temperatures below the ground surface that correspond to calculated temperatures at a particular location. If the temperatures agree, then the calculated earth temperatures can be passed along to the GIS engine for contour mapping and to dynamic rating systems for dynamic rating calculations. If the temperatures do not agree within a certain desired or allowable predetermined error value, then model earth property parameters may be adjusted to minimize the difference between the calculated and measured earth ambient temperature at the particular location. The process includes separating the soil thermal resistivity parameters from the soil volumetric heat capacity parameters. The thermal resistivity parameters are modified so the computed temperatures seek the magnitudes of the measured points and the heat capacity parameters are adjusted so the rate-of-change of the computed temperatures correspond to the rate-of-change of the measured points. The feedback loop can include sufficient dampening and dead band such that overshoot and oscillation does not occur.

Figure 6:
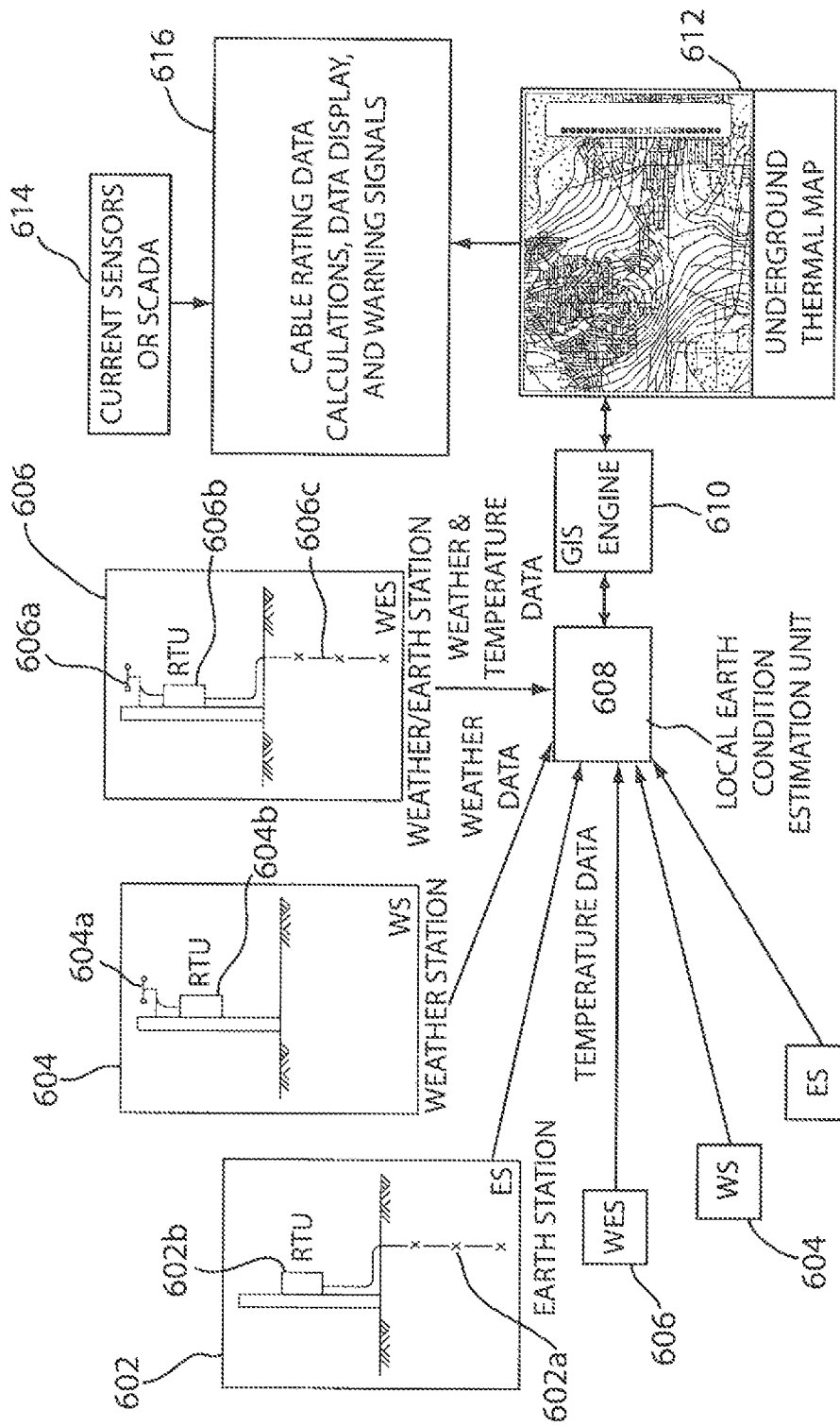
FIG. 6 is a system diagram showing a system organization and application.

Construction of a Weather-Based Wide Area Earth Thermal Condition Estimation System The wide area scheme is constructed of an array of monitoring stations. These will generally consist of weather and earth stations (WES), earth stations (ES) and weather stations (WS). The weather station may also be replaced by data streaming from weather data service providers if available. FIG. 6 illustrates an implementation of a weather-based wide area earth thermal condition estimation system. An ES 602 includes an earth tree 602a measuring subsurface temperatures at several depths that usually correspond to the maximum range of cable depths. A remote terminal unit 602b can be used to transmit the earth tree data to a local earth condition estimation unit 608. A WS 604 includes an air temperature sensor, a pyranometer—an actinometer also known as a solarimeter, an anemometer and a long wave radiation sensor measuring long wave radiation coming from both the sky and the earth 604a. A remote terminal unit 604b can be used to transmit the earth tree data to the local earth condition estimation unit 608. The WES 606 includes features of both WS 606a and ES instrumentation 606c. A remote terminal unit 606b can be used to transmit the earth tree data to a local earth condition estimation unit 608. At WES stations a more comprehensive dynamic modeling procedure can occur based on local data than can be obtained from either a ES or WS alone. At locations having an ES, the ES dynamic model obtains weather data from a nearby WS and WES stations. At locations having WS, the WS station completes dynamic analysis by obtaining updated soil parameters from a nearby WES and ES stations. In the WS based model the parameter adjustment feedback loop is disabled. In terms of sharing information, a system of weighting may be employed that ranks information based on (1) closeness or geophysical similarity of locations, and (2) strength or confidence of the calculated parameters, including soil volumetric heat capacity, soil thermal resistivity, and earth ambient temperature. The strength of the calculated parameters is highest for WES stations followed by ES and WE stations. Information from real-time commercial or government weather services such as SCADA 614 can also be integrated into the weather system data.

Figure 2:
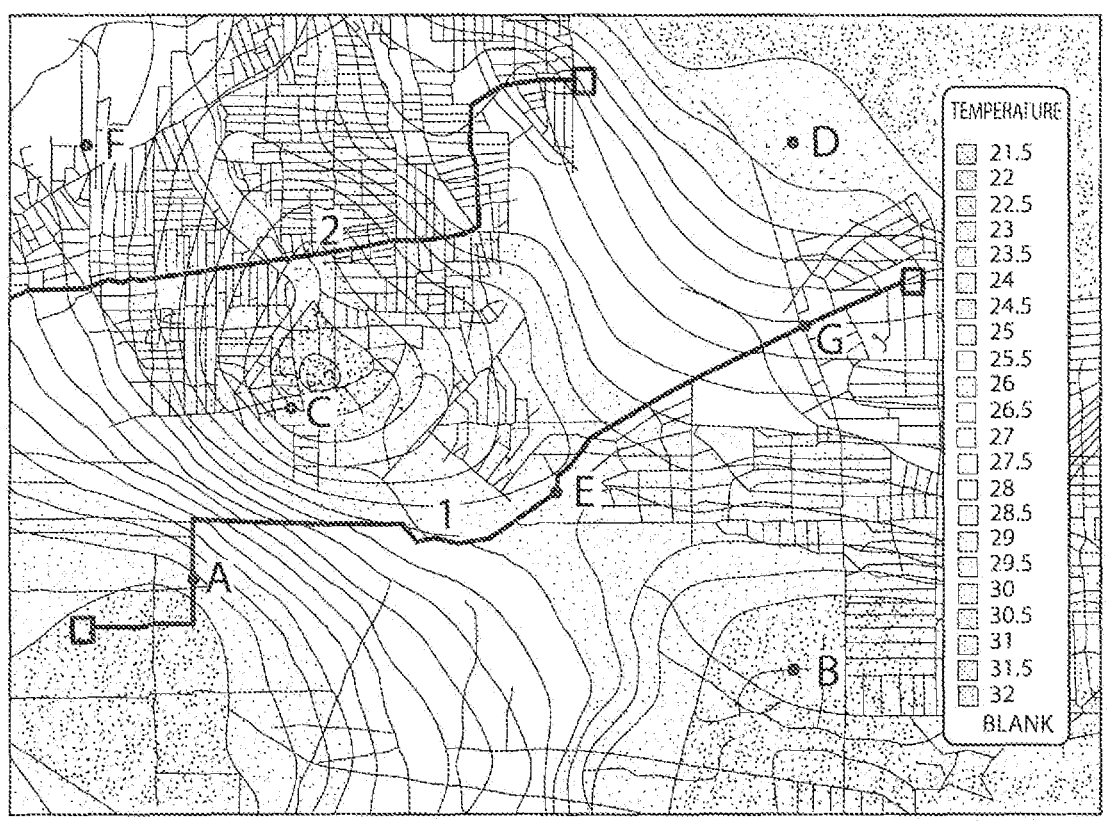
FIG. 2 is a diagram illustrating how earth conditions can be retrofitted for a route that does not have earth stations using measured weather data with the help of a Geographic Information System (GIS) engine.

Referring agains to FIG. 6, with these sensing locations (earth stations, weather stations, and/or earth-weather stations) installed in a wide area, the thermal properties and ambient temperatures at these locations can be determined. For the areas where there are no sensing locations, thermal properties and ambient temperature can be estimated by interpolating values from nearby measured locations. In this manner thermal condition data can be determined for a wide area. With map engines, such as a GIS engine 610, data can be displayed to form an underground thermal contour map 612 as shown in FIG. 2. Cable ratings for underground cables in the wide area network and resultant display and warning signals for such cables 616 can be cased on the calculated underground thermal contour map and available real-time commercial or government data.

Superposition of Heat Sources and Heat Sinks

Figure 7:
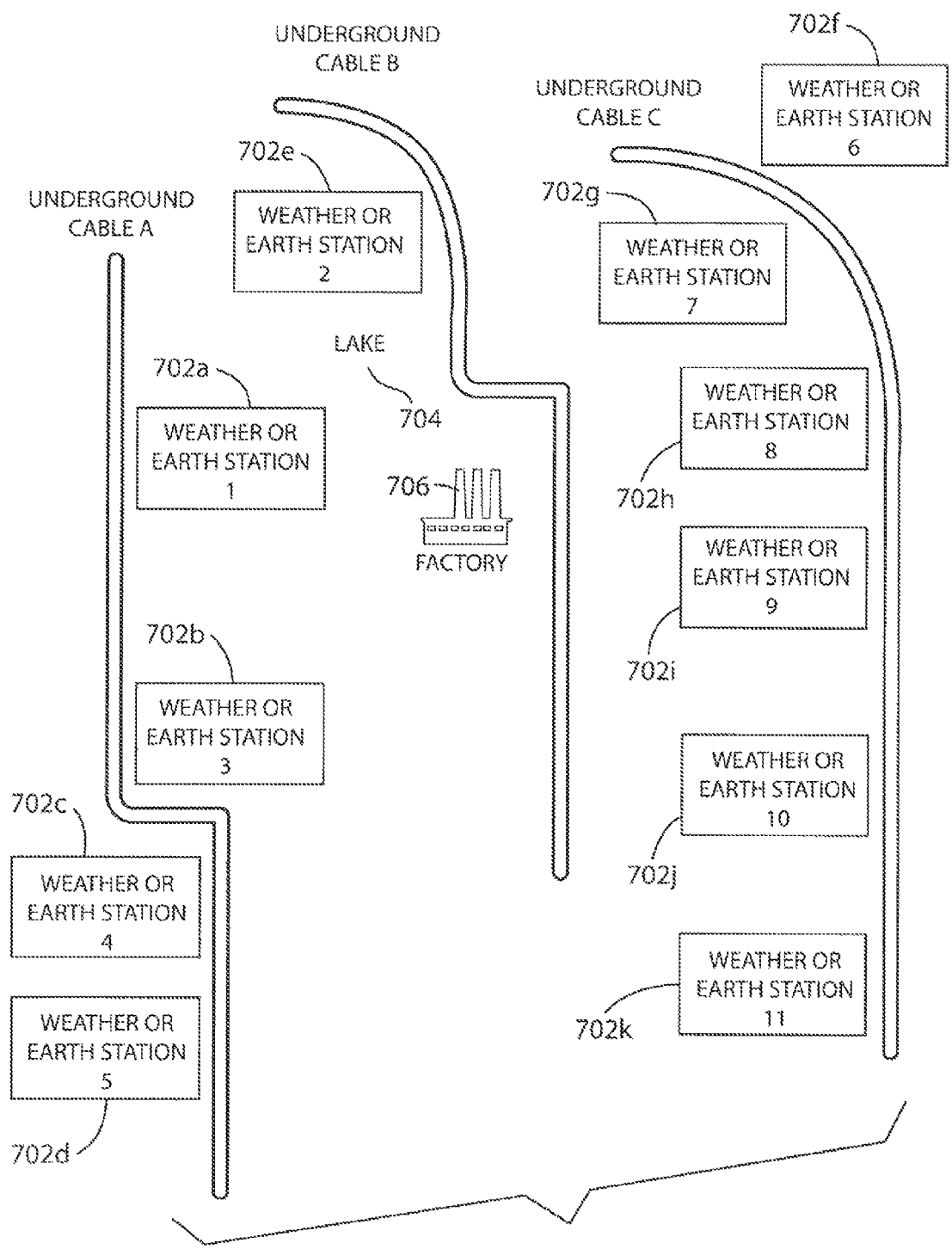
FIG. 7 is a diagram showing an area with additional heat sources and sinks Weather/earth stations are deployed for superimposing effect of heat sources/sinks on the system.

Referring to FIGS. 2 and 7, when constructing a real-time Weather-Based Wide Area Earth Thermal Condition 3-dimensional map factors such as additional heat sources—which tend to add heat, or heat sinks, which tend to remove heat, from an underground cable, also may be considered. Heat sources and sinks include, for example, other nearby cables, lakes, rivers, etc. The heat sources and heat sinks can affect the current carrying capacity of an underground cable. A heat source can heat up earth leading to a higher earth ambient temperature and higher soil thermal resistivity at affected areas whereas the heat sink can cool the earth leading to a lower earth ambient temperature and lower soil thermal resistivity. FIG. 7 illustrates three underground cables, Cable A, Cable B, and Cable C. To consider the effect of a heat source such as a cable, a weather station, earth station, or weather earth stations can be deployed at locations close to the cable. For example, each of Cables A-C has a number of WS, ES, or WES 702a , , , 702k at locations adjacent the respective cable runs. A WS, ES, or WES 702e is deployed near a lake 704 as the lake can affect the soil parameters associated with Cable B. In a similar manner, a WS, ES, or WES 702b is deployed at a location on Cable A that may affected by a nearby factory 706. With the real-time data from these stations, earth ambient temperatures can be measured and earth thermal properties can be determined using the algorithm described above and shown in FIG. 5. These results can be used as input to map engines and using the interpolation algorithm a revised real-time Weather-Based Wide Area Earth Thermal Condition map considering heat sources and heat sinks can be obtained. The same thing can be done to a heat sink such as a water pipe by deploying measurement stations at locations close to the water pipe for measuring affected earth ambient temperatures and establishing earth thermal properties. Subsequently utilizing the map engines and interpolation algorithm, the heat sources and heat sinks can be superimposed onto the Wide Area Earth 3-dimensional Thermal Condition map resulting in a real-time Weather-Based Wide Area Earth Thermal Condition map with the weather conditions as the driving force.

The 3-dimensional map displays both earth ambient temperatures and earth thermal properties dynamically in the wide area and can be used for power cable ratings and other applications. The 3-dimensional map may be used by utilities to help operators monitor their underground power systems in real-time. Wide-area thermal properties and ambient earth temperature data can also be used to calculate dynamic ampacity of underground power devices. When values of the thermal properties or ambient temperature exceed the predefined value, warning signals are created and sent to the controlling center to control possible damages.

Although preferred embodiments of the present invention thereof have been disclosed and described in details herein, it is to be understood that this invention is not limited to those precise embodiments. Other modifications and variations may be effected by one skilled in the art without departing from the spirit and scope of the invention as define by the appended claims.

We claim:

1. A method of determining earth sub-surface thermal characteristics over an area, comprising:
   receiving real-time weather data and earth data measured at a plurality of locations associated with an underground electrical cable;
   calculating earth thermal properties at each of the plurality of locations based on the real-time weather data and the earth data by an iterative process;
   interpolating the calculated earth thermal properties at two or more of the plurality of locations to determine interpolated earth thermal properties at another location associated with the underground electrical cable; and
   creating a wide-area thermal property map from at least some of the calculated earth thermal properties and the interpolated earth thermal properties.

2. The method of claim 1, further comprising:
   superimposing known heat sources and heat sinks affecting the earth thermal properties associated with the underground electrical cable into the wide-area thermal property map; and
   continuously providing real-time weather data and earth data measured in the vicinity of the known heat sources and heat sinks such that the wide-area thermal property map is a wide-area dynamic thermal 3-dimensional map of earth thermal properties at depths at the plurality of locations.

3. The method of claim 2, further comprising:
   calculating underground electrical cable power ratings including safe current carrying ampacities that are less than a predetermined threshold based on the wide-area dynamic 3-dimensional map; and
   wherein warning signals are generated when the calculated earth thermal properties change in accordance with changes in the real-time weather data and the earth data by an amount that affects the safe current carrying ampacity of the underground electrical cable.

4. The method of claim 3, wherein the earth thermal properties include soil volumetric heat capacity and soil thermal resistivity.

5. The method of claim 2, wherein the iterative process comprises, for one or more selected locations from the plurality of locations:
   (a) calculating earth ambient temperature data based on values of earth thermal properties and the real-time weather data at the one or more selected locations;
   (b) receiving real-time measured earth ambient temperature from earth ambient temperature measurement devices at the one or more selected locations;

(c) comparing the calculated earth ambient temperature data with the measured earth ambient temperature data at each of the one or more selected locations;

(d) determining an error value based on the comparing step at each of the one or more selected locations;

(e) adjusting values for the earth thermal properties at each of the one or more selected locations based on the determined error value;

(f) re-calculating the calculated earth ambient temperature data from the real-time weather data and the adjusted values for earth thermal properties at each of the one or more selected locations;

(g) repeating steps (c) to (f) until the error value is within a predetermined value at each of the one or more selected locations.

6. The method of claim 5, wherein the earth thermal properties include soil volumetric heat capacity and soil thermal resistivity.

7. The method of claim 4, wherein the received earth data includes earth ambient temperature measurements from an earth tree or from distributed temperature sensors distributed along the electrical cable.

8. The method of claim 7, comprising:
identifying soil hot spot locations using the distributed temperature sensors; and
installing an earth tree of point temperature sensors at the identified hot spot locations to determine earth temperatures at different depths of the identified hot spot locations.

9. The method of claim 1, wherein the real-time weather data and earth data are received from weather stations or weather data service providers.

10. The method of claim 1, wherein real-time weather data includes wind speed, solar radiation, earth surface temperature, and rainfall.

11. The method of claim of claim 5, wherein the calculated earth thermal properties at two or more of the plurality of locations are weighted based on
(a) whether the real-time data are received from a weather station measuring properties, including air temperature, wind speed, solar radiance and long wave radiation, an earth station measuring earth ambient temperature, or a weather earth station to determine interpolated earth thermal properties at the another location, and
(b) whether the earth thermal properties at the another location are similar to the earth thermal properties at each of the two or more of the plurality of locations.

12. The method of claim 1, further comprising passing the calculated earth thermal properties to a dynamic rating system for calculating real-time power cable ratings.

* * * * *